(12) United States Patent
Hong et al.

(10) Patent No.: US 6,187,121 B1
(45) Date of Patent: Feb. 13, 2001

(54) DIE-BONDING EQUIPMENT AND A METHOD FOR DETECTING RESIDUAL ADHESIVE MATERIAL USING THE SAME

(75) Inventors: Sung-bok Hong; Yong-choul Lee; Yong-dae Ha; Young-gon Hwang, all of Chungcheongnam-do (KR)

(73) Assignee: Samsung Electronics Co., Ltd. (KR)

( * ) Notice: Under 35 U.S.C. 154(b), the term of this patent shall be extended for 0 days.

(21) Appl. No.: 09/187,353

(22) Filed: Nov. 6, 1998

(30) Foreign Application Priority Data

Nov. 25, 1997 (KR) .................................................. 97-62581

(51) Int. Cl.[7] ........................................................ B32B 35/00
(52) U.S. Cl. .............................. 156/64; 156/378; 156/379
(58) Field of Search ............................ 156/64, 378, 379, 156/360; 356/394, 397, 401, 399, 400; 118/713, 669, 712; 382/145, 150, 149, 146

(56) References Cited

U.S. PATENT DOCUMENTS

| | | | |
|---|---|---|---|
| 3,909,602 | * | 9/1975 | Micka .......................................... 716/4 |
| 5,908,150 | * | 6/1999 | Miura ..................................... 228/102 |

* cited by examiner

Primary Examiner—Richard Crispino
Assistant Examiner—George R Koch, III
(74) Attorney, Agent, or Firm—Skjerven Morrill MacPherson; David T. Millers

(57) ABSTRACT

Die-bonding equipment and a method for detecting adhesive dotting on a substrate are disclosed. A dotted adhesive pattern illustrating an actually dotted state of the adhesive on a substrate is overlap-photographed with a standard pattern illustrating proper dotting pattern. The overlap-photographed pattern is compared with a standard overlap pattern. According to the compared result, whether the adhesive is properly dotted on the substrate is decided. When the adhesive is not properly dotted, an alarm signal is generated.

23 Claims, 6 Drawing Sheets

DIE-BONDING EQUIPMENT AND A METHOD FOR DETECTING RESIDUAL ADHESIVE MATERIAL USING THE SAME

BACKGROUND OF THE INVENTION

1. Field of the Invention

The present invention relates to die-bonding equipment and methods for detecting whether an adhesive such as Ag-epoxy is properly dotted on a die pad of a lead frame or a substrate, enabling timely replacement of adhesive tubes and preventing poor bonding of a semiconductor chip to the die pad.

2. Description of the Related Art

Generally, an assembly process of semiconductor packages includes: dicing of a wafer including a number of semiconductor chips into individual semiconductor chips; bonding of each semiconductor chip on a die pad of a lead frame using an adhesive; wire-bonding to connect the bonding pads of the semiconductor chip to inner leads of the lead frame; encapsulation of the semiconductor chip, the wire and the inner leads with a molding compound to protect the semiconductor chip from the external environment; singulation of each individual package and forming outer leads of the lead frame; and marking of a trademark and a product serial number on the package.

In the die-bonding process, the lead frame is placed at a predetermined position by a transferring unit, and an adhesive is dotted on the die pad of the lead frame by a dispenser in the die-bonding equipment. Then, a bonding-head picks up a semiconductor chip and attaches the backside of the semiconductor chip to the die pad. The final step of the die-bonding process is curing of the adhesive.

Ag-epoxy adhesive is commonly used as an adhesive between a die pad and a semiconductor chip. In the die-bonding equipment, Ag-epoxy adhesive contained in a tube is loaded in a dispenser. When the tube is empty or nearly empty, an operator of the apparatus replaces the tube with a new tube.

To select when to replace the tube, the operator loads a new adhesive tube, and sets a controlling unit with an expected number of dotting operation from the tube. When operating, the equipment counts actual adhesive dotting, and when the count is the same as the set number, the control unit alerts operator to inform the operator that the presently used tube is running out of the adhesive and needs to be replaced with a new one. Thus, the operator replaces the adhesive tube according to the number of dottings, not according to the state of adhesive dotting on the die pad. Generally, the operator changes the expected number of dottings according to the size of semiconductor chips because larger chips need more adhesive for die bonding. However, the expected number set by the operator can be incorrect due to a miscalculation of the chip size and adhesive use at an expected rate, or human error in setting the expected number. The set number being incorrect can result in waste of adhesive if tubes are changed too often or improper bonding if tubes are changed too infrequently.

SUMMARY OF THE INVENTION

In accordance with an aspect of the present invention, a die-bonding equipment detects the state of adhesive dotted on a die pad of a lead frame or a substrate using a camera and determines when the adhesive tube being used should be replaced with a new one.

One embodiment of die-bonding equipment according to the present invention includes: a loading unit for loading a lead frame or a substrate; dispenser for dotting an adhesive on a die pad of the lead frame or the substrate; an adhesive detecting unit; a bonding head unit for picking up a semiconductor chip and attaching the semiconductor chip to the die pad; and an unloading unit for unloading the lead frame or the substrate with the semiconductor chip attached thereto.

The adhesive detecting unit includes: an overlapped pattern forming unit for overlap-photographing a pattern of adhesive dots on the die pad of the lead frame or the substrate and a standard pattern for the dots; a determining unit for determining whether the adhesive is properly dotted; and a controlling unit for displaying the result on an output unit and/or generating an alarm signal to inform the operator that the adhesive is not properly dotted.

A first embodiment of the overlapped pattern forming unit includes: a body; a semitransparent member; a standard pattern forming unit; a camera unit for photographing a dotted adhesive pattern and the standard pattern projected on the semitransparent member; and a light-emitting unit for providing light for camera.

The components of the overlapped pattern forming unit can be placed inside the unit in various ways for proper overlap-photographing of the dotted adhesive pattern and the standard adhesive pattern. Additional components can also be included in the overlapped pattern forming unit to accomplish the same purpose.

The present invention also provides a method for detecting adhesive dotted on a die pad of a lead frame or a substrate. The method comprises the steps of: overlap-photographing of a standard pattern and an adhesive pattern dotted on the die pad; reading and inputting of the standard pattern; subsequent reading and inputting of the dotted adhesive pattern; evaluating the degree of overlap between the standard pattern and the dotted adhesive pattern; and generating an alarm signal when the evaluation shows that the adhesive is not properly dotted.

Therefore, the present invention can enable a timely notice of adhesive tube replacement and prevent poor die bonding caused by an improper adhesive dispensing.

BRIEF DESCRIPTION OF THE DRAWINGS

The advantages of the present invention will become more apparent by describing embodiments thereof with reference to the accompanying drawings, in which.

DETAILED DESCRIPTION OF THE PREFERRED EMBODIMENTS

The present invention now will be described more fully hereinafter with reference to the accompanying drawings. This invention may be embodied in many different forms and should not be construed as limited to the embodiments set forth herein; rather, these embodiments are provided so that this disclosure will be thorough and complete, and will convey the invention to those having skill in the art.

Figure 1:
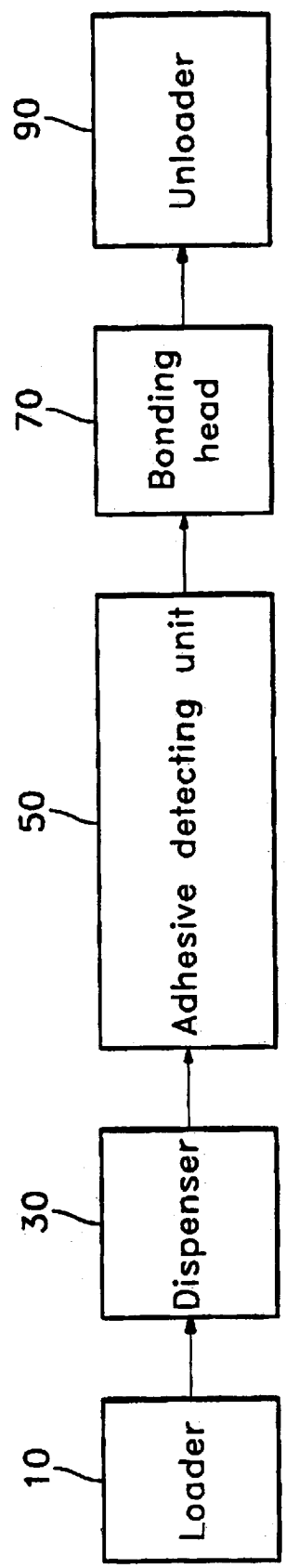
FIG. 1 is a schematic block diagram of a die-bonding equipment according to an embodiment of the present invention.

FIG. 1 is a schematic block diagram of a die-bonding equipment according to the present invention. As shown in FIG. 1, the die-bonding equipment includes: a loader 10 for loading a lead frame to be subjected to a die-bonding process; a dispenser 30 for dotting adhesive, for example, Ag-epoxy, on a die pad of the lead frame; an adhesive detecting unit 50 for deciding whether the adhesive was properly dotted on the die pad; a bonding head 70 for picking up a semiconductor chip and attaching the semiconductor chip to the die pad; and an unloader 90 for unloading the lead frame with the semiconductor chip bonded thereto.

Figure 2:
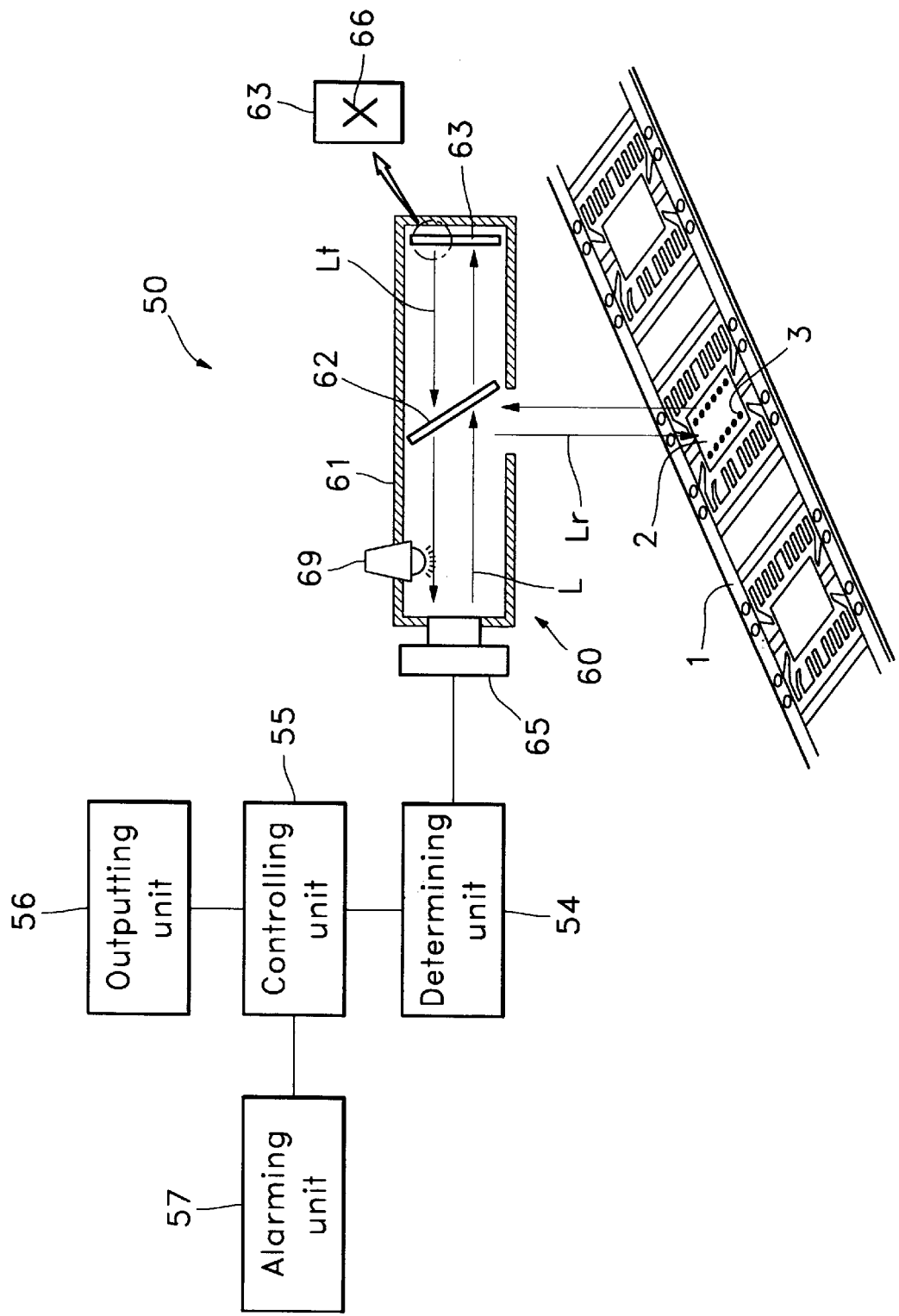
FIG. 2 is a schematic diagram of an embodiment of an adhesive detecting unit of FIG. 1.
Figure 3A:
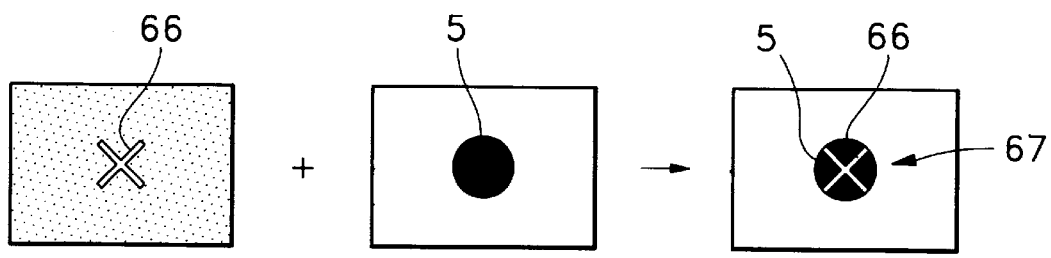
FIG. 3A is a block diagram illustrating a dotted state detecting process according to the present invention, wherein an adhesive is dotted.
Figure 3B:
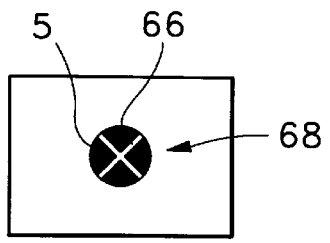
FIG. 3B is a block diagram illustrating a pre-inputted overlapped pattern.

Referring to FIGS. 2, 3A and 3B, the adhesive detecting unit 50 will be described in detail. As shown in FIGS. 2, 3A and 3B, an overlapped pattern forming unit 60 photographs a dotted adhesive pattern 5 and a standard pattern 66 and transfers image signals corresponding to patterns 5 and 66 to a determining unit 54. In FIG. 3A, dotted adhesive pattern 5 is a circular dot of adhesive dotted on a die pad 2 of a lead frame 1 by a dispenser 30. The standard pattern 66 is an X-shaped mark that has the correct relative location and size for adhesive pattern 5 on die pad 2 of lead frame 1. Accordingly, when adhesive pattern 5 is correctly formed, standard pattern 66 and dotted adhesive pattern 5 are located in the overlapped image at the same coordinates.

Determining unit 54 compares the image signals supplied from overlapped pattern forming unit 60 with an image signal of a pre-inputted reference pattern 68, and evaluates the adhesive dotting. In other words, determining unit 54 decides whether an overlapped pattern 67 formed by overlapping dotted adhesive pattern 5 and standard pattern 66 as shown in FIG. 3A is the same as pre-inputted reference pattern 68 in FIG. 3B. According to the result from determining unit 54, a controlling unit 55 activates an alarm 57 which generates an alarm signal to inform an operator that the adhesive tube used in the equipment needs to be replaced with a new one. The image signal generated from the overlapped pattern forming unit 60 is outputted as an image on an outputting unit 56, e.g., a monitor, through controlling unit 55.

As shown in FIG. 2, overlapped pattern forming unit 60 includes: a body 61; a semitransparent member, for example, a half-silvered mirror 62, which is in body 61 facing at about a 45° angle with die pad 2; a standard pattern forming unit 63 installed at an end in the body 61 spaced apart from half-silvered mirror 62 and including standard pattern 66 formed thereon; a camera unit 65 installed at the other end of body 61 spaced apart from half mirror 62, for simultaneously photographing standard pattern 66 and dotted adhesive pattern 5 as projected via half-silvered mirror 62; and a light-emitting unit 69, for example, a lamp, for providing light into body 61 in the direction from camera unit 65 to half mirror 62.

Half-silvered mirror 62 has a light transmissivity of approximately 45 to 55%, preferably, 50%. Half-silvered mirror 62 is installed in body 61 at an angle of 45 degrees with respect to die pad 2 so that dotted adhesive pattern 5 can be viewed via reflection from a surface of half-silvered mirror 62 and standard pattern 66 can be viewed via transmission through mirror 62.

In addition, the distance between lead frame 1 and mirror 62 is the same as the distance between half mirror 62 and standard pattern forming unit 63. In the event that one of the above distances changes according to the focus of camera unit 65, the other distance also changes to be the same as the first distance. Preferably, the distances may be approximately 4 to 5 cm.

A charge-coupled device (CCD) camera is used as camera unit 65.

Standard pattern forming unit 63 is made of a reflecting material on which standard pattern 66 is formed. As shown in FIG. 2, standard pattern 66, i.e., an X-shaped mark for a dot of adhesive 3, is formed on an area of standard pattern forming unit 63 corresponding to an area of dotted adhesive pattern 5 on die pad 2. Even though standard pattern 66 of this embodiment is an X-shaped mark, standard pattern 66 can be modified to have rectangular, triangular or circular shape that matches the size of pattern 5. Additionally, since it is preferable that standard pattern forming unit 63 have the same reflectivity as lead frame 1, both standard pattern forming unit 63 and lead frame 1 can be made of the same material. Generally, a lead frame formed of alloy, e.g., Cu-alloy, or a lead frame of Cu is used for the standard pattern forming unit 63.

Figure 5:
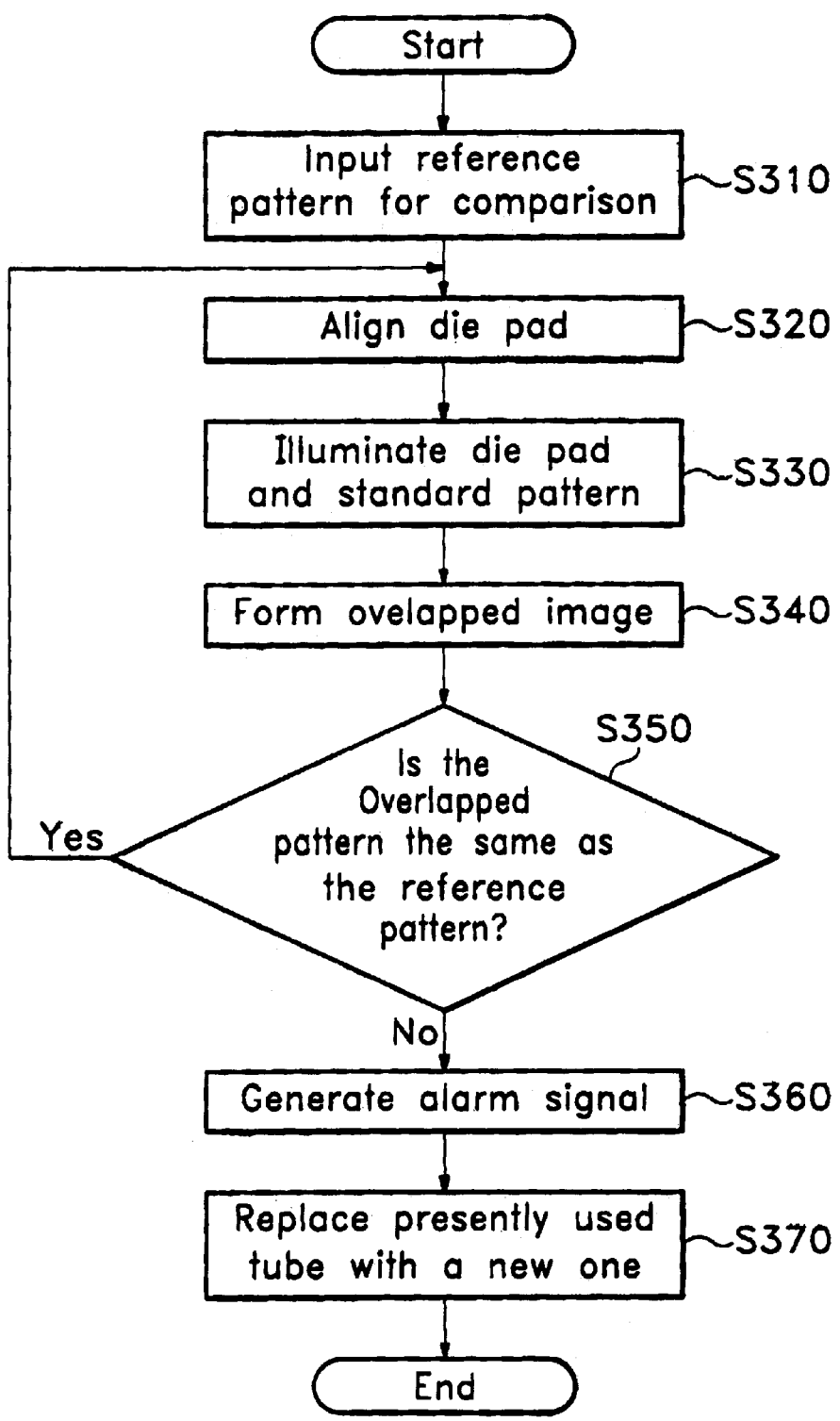
FIG. 5 is a flow chart of a method for detecting adhesive according to an embodiment of the present invention.

The method for detecting dotted adhesive pattern 5 by adhesive detecting unit 50 will be described with reference to FIGS. 2 and 5. FIG. 5 is a schematic flowchart of the method.

First, a reference pattern 68 that is the expected overlap of standard pattern 66 and dotted pattern 5 is inputted to determining unit 54. (step S310)

After adhesive dotting by dispenser 30, lead frame 1 is moved until die pad 2 is located and aligned under adhesive detecting unit 50. The alignment of die pad 2 can be properly achieved in the same way that a conventional die-bonding equipment aligns. Thereafter, light-emitting unit 69 provides light L into body 61. A part of light L, which is designated as Lt, passes through half-silvered mirror 62, and another part of light L, which is designated as Lr, reflects from half-silvered mirror 62.

When light Lt reflects from standard pattern forming unit 63, standard pattern 66 is projected on a back surface of mirror 62 and is partially transmitted through mirror 62 to camera unit 65. Camera unit 65 photographs the projected standard pattern, and controlling unit 55 produces an image signal corresponding to the projected standard pattern. Light Lr reflects from die pad 2, back to mirror 62 and partially reflects from mirror 62 to camera 65. Accordingly, camera 65 simultaneously receives light from standard pattern forming unit 63 and die pad 2. (step S330) Camera unit 65 photographs overlapping images of dotted adhesive pattern 5 and standard pattern 66, and controlling unit 55 produces an image signal corresponding to the overlapping images. Outputting unit 56 displays overlapped images 67. (step S340)

Determining unit 54 evaluates the degree of deviation of overlapped pattern 67 from pre-inputted reference pattern 68, and decides whether the degree of the deviation is negligible, that is, whether overlapped pattern 67 is the same as pre-inputted reference pattern 68. (step S350)

When determining unit 54 determines that the overlapped patterns 67 is not the same as pre-inputted reference pattern 68, alarm 57 generates an alarm signal for indicating that the adhesive dotting on die pad 2 is not proper. (step S360) Then, an operator stops the operation of die bonding equipment and replaces the currently used adhesive tube (not shown) with a new one. (step S370)

Referring to FIGS. 3A, 3B, 4A and 4B, the process of displaying the images corresponding to patterns 5, 66, 67 and 68 on outputting unit 56 will be described in detail.

When outputting unit 56 displays dotted adhesive pattern 5, dotted adhesive pattern 5 appears as black and the other area appears as white, as shown in FIG. 3A. X-shaped standard pattern 66 is displayed as white and the other area is displayed as black on outputting unit 56 as shown in FIG. 3A. As aforementioned, standard pattern 66 may also have rectangular, triangular or circular shape. In this embodiment of the present invention will be described using X-shaped standard pattern 66.

When dotted adhesive pattern overlaps standard pattern 66, the white X mark of standard pattern 66 overlaps black dotted adhesive pattern 5, and overlapped pattern 67 is displayed on outputting unit 56. By monitoring displayed overlapped pattern 67, the operator can determine whether adhesive 3 is properly dotted on die pad 2.

Figure 4A:
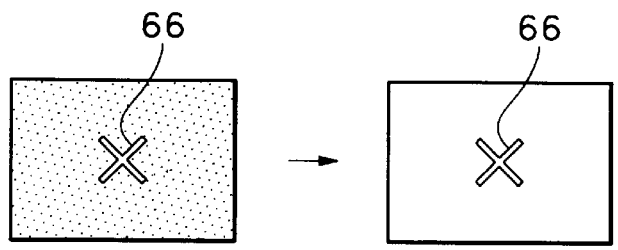
FIG. 4A is a block diagram illustrating a dotted state detecting process according to the present invention, wherein an adhesive is not dotted.
Figure 4B:
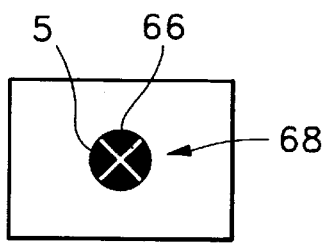
FIG. 4B is a block diagram illustrating a pre-inputted overlapped pattern.

For example, in the event that adhesive 3 is not dotted on die pad 2 due to complete consumption of adhesive in the tube presently used, overlapped pattern appears on outputting unit 56 as shown in FIG. 4A. In this case, the resulted overlapped pattern in FIG. 4A is different from pre-inputted reference pattern 68 in FIG. 4B. Then, controlling unit 55 produces an alarm signal using alarm 57 to inform the operator of the complete consumption of the adhesive tube. Accordingly, after checking the overlapped pattern displayed on outputting unit 56, the operator replaces the consumed adhesive tube with a new one.

Figure 6:
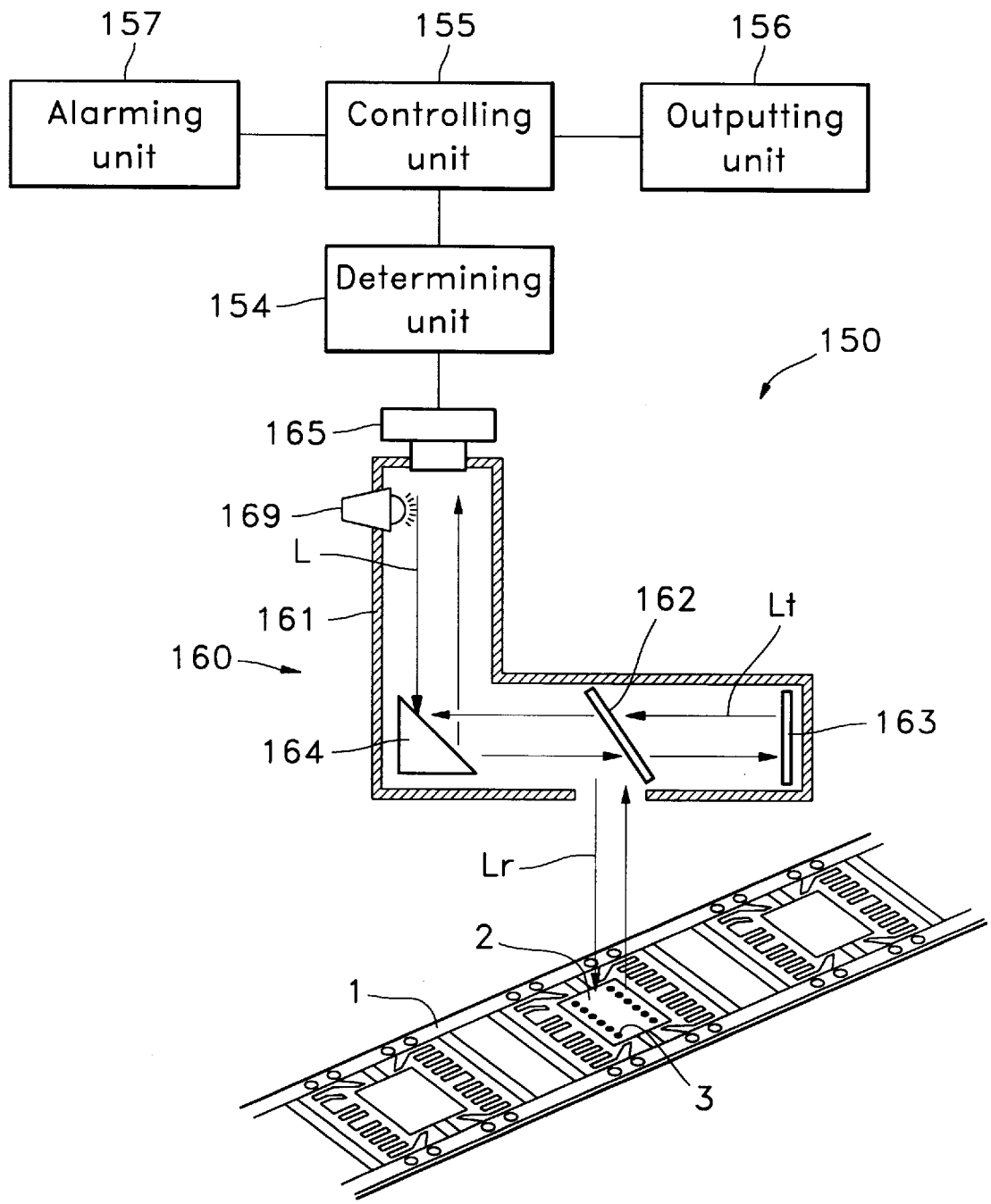
FIG. 6 is a schematic diagram of another embodiment of an adhesive detecting unit according to the present invention.

FIG. 6 is a schematic diagram of another embodiment of an adhesive detecting unit according to the present invention.

As shown in FIG. 6, adhesive detecting unit 150 has a reflecting mirror 164 in addition to the same elements as adhesive detecting unit 50 in FIG. 2. Detecting unit 150 also includes a modified overlapped pattern forming unit 160, a determining unit 154, a controlling unit 155 and an outputting unit 156. Modified overlapped pattern forming unit 160 will be described.

As shown in FIG. 6, overlapped pattern forming unit 160 includes: a body 161; a semitransparent member, for example, a half-silvered mirror 162, which is installed in body 161 facing at a 45° angle with die pad 2 having adhesive dotted thereon; a standard pattern forming unit 163 installed at an end in body 161 spaced apart from half-silvered mirror 162 and including a standard pattern formed thereon; a reflecting member, for example, a reflecting mirror 164, installed in body 161, for reflecting a dotted adhesive pattern and the standard pattern projected to half mirror 162; a camera unit 165 installed at the other end of body 161 for photographing the dotted adhesive pattern and the standard pattern reflected from reflecting mirror 164; and a light-emitting unit 169, for example, a lamp, for providing light into body 161 in the direction from camera unit 165 to half mirror 162.

Half-silvered mirror 162 has a light transmissivity of approximately 45% to 55%, preferably, 50%. Half-silvered mirror 162 is installed in body 161 at an angle of 45 degrees with respect to die pad 2 so that dotted adhesive pattern is projected to one surface of half-silvered mirror 162 and the standard pattern is projected to the other surface thereof. The installation angle the half-silvered mirror 162 is the same as the slanting angle of reflecting mirror 164.

Overlapped pattern forming unit 160 has the same structure as the previously described overlapped pattern forming unit 60 except for the fact that the standard pattern and the dotted adhesive pattern projected to half-silvered mirror 162 are photographed by camera unit 165 through reflecting mirror 164. Of course, adhesive detecting unit 150 including overlapped pattern forming unit 160 may be also used without any degradation of efficiency compared to adhesive detecting unit 50 including overlapped pattern forming unit 60.

Figure 7:
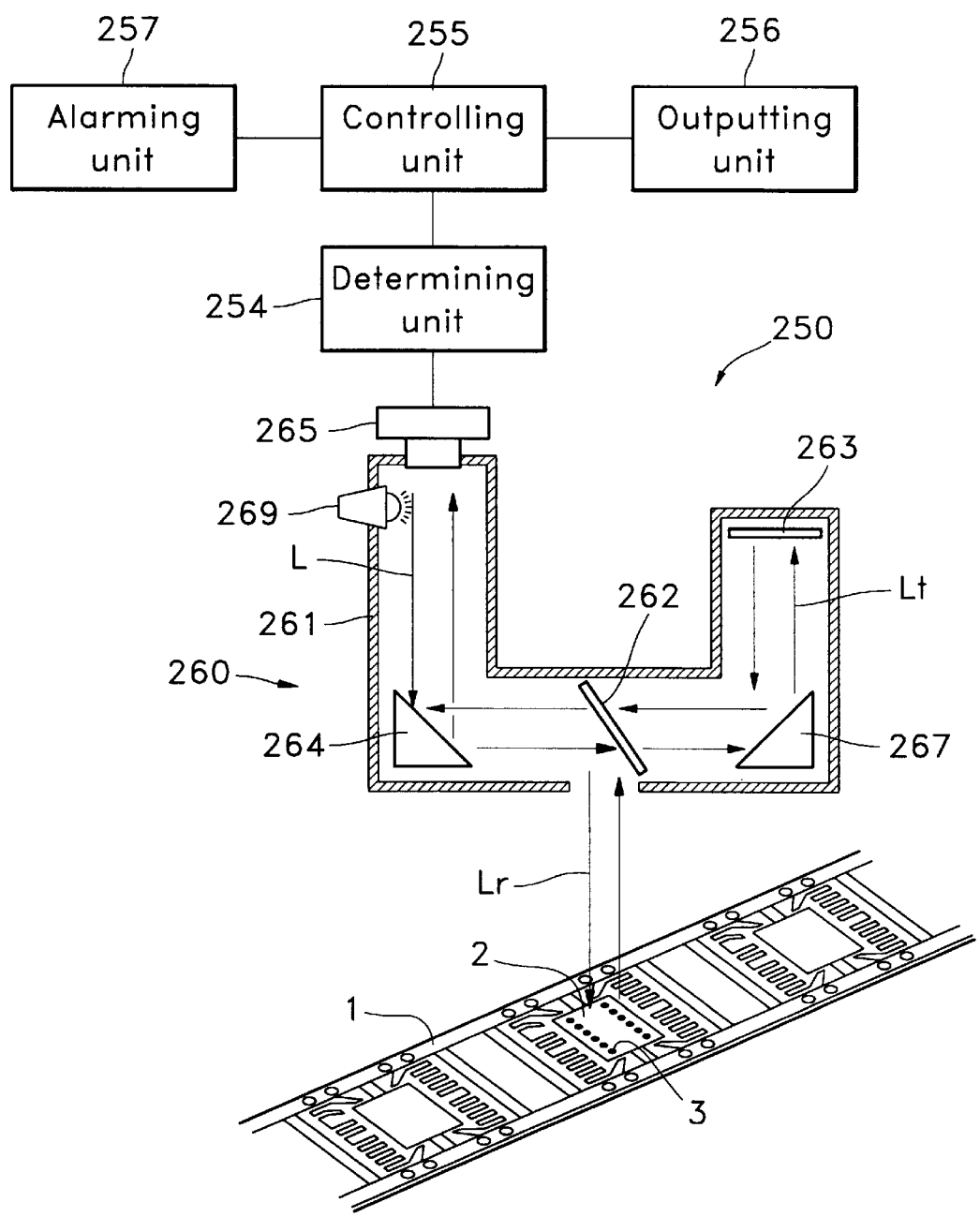
FIG. 7 is a schematic diagram of still another embodiment of an adhesive detecting unit according to the present invention.

FIG. 7 is a schematic diagram of another embodiment of an adhesive detecting unit according to the present invention.

As shown in FIG. 7, adhesive detecting unit 250 includes reflecting mirrors 264 and 267 in addition to the same elements as previously described adhesive detecting unit 50 in FIG. 2. The detecting unit 250 includes an overlapped pattern forming unit 260, determining unit 254, a controlling unit 255 and an outputting unit 256. Since adhesive detecting unit 250 is different from adhesive detecting unit 50 only in the structure of overlapped pattern forming units 60 and 260, overlapped pattern forming unit 260 will be described in detail.

As shown in FIG. 7, overlapped pattern forming unit 260 includes: a body 261; a semitransparent member, for example, a half-silvered mirror 262, which is installed in body 261 facing at a 45° angle with die pad 2 having adhesive dotted thereon; a first reflecting mirror 264 installed in body 261 spaced apart from one surface of half-silvered mirror 262 and having a reflecting surface slanted at an angle for reflecting a dotted adhesive pattern projected on half mirror 262; a second reflecting mirror 267 installed in body 261 spaced apart from the other surface of half-silvered mirror 262 and having a reflecting surface slanted at an angle; a standard pattern forming unit 263 installed in body 261 and including a standard pattern formed thereon; a camera unit 265 for photographing the dotted adhesive pattern and the standard pattern reflected from first reflecting mirror 264; and a light-emitting unit 269, for example, a lamp, for providing light into body 261 in the direction from camera unit 265 to half-silvered mirror 262. Overlapped pattern forming unit 260 is the same as overlapped pattern forming unit 160 except for the fact that the standard pattern is reflected on second reflecting member 267 and projected to half-silvered mirror 262.

Of course, adhesive detecting unit 250 including overlapped pattern forming unit 260 may be used without degradation of efficiency compared to detecting units 50 and 150 including the overlapped pattern forming units 60 and 160.

In summary, the present invention enables: 1) timely replacement of adhesive tube in die bonding; and 2) detection of improper adhesive dotting. Further, the timely replacement prevents adhesive wasting caused when a used adhesive tube is replaced with a new one even though a considerable amount of adhesive still remains in the used tube. By detecting improper adhesive dotting, the present invention also prevents production of potentially unreliable semiconductor packages due to the die bonding with the improper adhesive dotting.

This invention has been described above with reference to the aforementioned embodiments. It is evident, however, that many alternatives, modifications and variations will be apparent to those having skill in the art in light of the foregoing description. Accordingly, the present invention embraces all such alternatives, modifications and variations as fall within the spirit and scope of the appended claims.

What is claimed is:

1. Die-bonding equipment comprising:
    a dispenser for dotting an adhesive on a die pad of a substrate; and
    an adhesive detecting unit for detecting whether the adhesive is properly dotted on the die pad by forming an overlapped pattern of a dotted adhesive pattern of the adhesive and a standard pattern, and by comparing an overlapped pattern with a preset reference pattern.

2. The die-bonding equipment according to claim 1, wherein the adhesive detecting unit comprises:
    means for forming the overlapped pattern using the dotted pattern of the adhesive and the standard pattern;
    a determining unit for receiving an image signal corresponding to the overlapped pattern from the means for forming the overlapped pattern, and determining whether the adhesive is properly dotted on the die pad by comparing the image signal corresponding to the overlapped pattern with an image signal corresponding to the preset pattern; and
    a controlling unit for receiving a result determined by the determining unit and controlling the die-bonding process according to the result.

3. The die-bonding equipment according to claim 2, wherein the adhesive detecting unit further comprises an alarm that generates an alarm signal through the controlling unit according to the result determined by the determining unit.

4. The die-bonding equipment according to claim 2, wherein the means for forming the overlapped pattern comprises:
    a body;
    a semitransparent member installed in the body facing slantways the die pad with the adhesive dotted thereon at an angle and having a light transmissivity;
    a standard pattern forming unit installed at an end of the body spaced apart from the semitransparent member and including the standard pattern formed thereon;
    a camera unit installed at the other end in the body spaced apart from the semitransparent member, for photographing the dotted adhesive pattern and the standard pattern projected on the semitransparent member; and
    a light-emitting unit for providing light into the body in a direction from the camera unit to the semitransparent member.

5. The die-bonding equipment according to claim 4, wherein the semitransparent member is a half mirror having the light transmissivity.

6. The die bonding equipment according to claim 5, wherein the light transmissivity is ranged from approximately 45% to 55%.

7. The die-bonding equipment according to claim 6, wherein the light transmissivity is 50%.

8. The die-bonding equipment according to claim 4, wherein the semitransparent member has a surface on which the dotted adhesive pattern is projected and an opposite surface on which the standard pattern is projected.

9. The die-bonding equipment according to claim 8, wherein the semitransparent member is slanted at an angle of 45 degrees with respect to the die pad.

10. The die-bonding equipment according to claim 4, wherein a distance between the semitransparent member and the standard pattern forming unit is changed according to a distance between the lead frame and the semitransparent member.

11. The die-bonding equipment according to claim 10, wherein the distance between the semitransparent member and the standard pattern forming unit is equal to the distance between the lead frame and the semitransparent member.

12. The die-bonding equipment according to claim 11, wherein the distance between the semitransparent member and the standard pattern forming unit is 4 to 5 cm.

13. The die-bonding equipment according to claim 4, wherein the standard pattern forming unit is a reflecting member on which a standard pattern is formed.

14. The die-bonding equipment according to claim 13, wherein the reflecting member has the same reflectivity as the die pad.

15. The die-bonding equipment according to claim 13, wherein the reflecting member is made of Cu-alloy.

16. The die-bonding equipment according to claim 2, wherein the means for forming the overlapped pattern comprises:
    a body;
    a semitransparent member installed in the body facing slantways the die pad with the adhesive dotted thereon at an angle and having a light transmissivity;
    a standard pattern forming unit installed in the body spaced apart from the semitransparent member and including the standard pattern formed thereon;
    a reflecting member installed in the body and having a reflecting surface slanted at an angle, for reflecting the dotted adhesive pattern and the standard pattern projected to the semitransparent member at an angle;
    a camera unit for photographing the dotted adhesive pattern and the standard pattern reflected from the reflecting member; and
    a light emitting unit for providing light into the body in a direction from the camera unit to the semitransparent member.

17. The die-bonding equipment according to claim 16, wherein the semitransparent member is installed at an angle which is equal to a slanting angle of the reflecting surface of the reflecting member.

18. The die-binding equipment according to claim 2, wherein the means for forming the overlapped pattern comprises:
    a body;
    a semitransparent member installed in the body facing slantways the die pad with the adhesive dotted thereon at an angle and having a light transmissivity;
    a first reflecting member installed in the body spaced apart from the semitransparent member and having a reflecting surface slanted at an angle, for reflecting the dotted adhesive pattern and the standard pattern projected on the semitransparent member;
    a second reflecting member installed in the body spaced apart from the semitransparent member in such a manner that the semitransparent member can be located between the first and second reflecting members, and having a reflecting surface slanted at an angle, for reflecting the standard pattern to the semitransparent member;
    a standard pattern forming unit installed in the body and including the standard pattern formed thereon, the standard pattern being reflected from the second reflecting member and projected on a surface of the semitransparent member;

a camera unit for photographing the dotted adhesive pattern and the standard pattern reflected from the first reflecting member; and a light-emitting unit for providing light into the body in a direction from the camera unit to the semitransparent member.

19. The die-bonding equipment according to claim 1, wherein the substrate is a lead frame.

20. The die-bonding equipment according to claim 1, wherein the substrate is a printed circuit board.

21. The die-bonding equipment according to claim 1, further comprising:

a loading unit for loading a substrate to be subjected to a die-bonding process;

a bonding head unit for picking up a semiconductor chip and attaching the semiconductor chip on the die pad dotted with the adhesive; and an unloading unit for unloading the substrate with the semiconductor chip attached thereto.

22. A method for detecting an adhesive dotted on a substrate, the method comprising:

measuring a pattern of the adhesive on the substrate;

forming an overlapped pattern which includes a standard pattern overlapped with the pattern of the adhesive on the substrate;

comparing the overlapped pattern to a reference overlapped pattern representing a overlapped pattern of the standard pattern and a properly dotted adhesive pattern;

determining from the comparison whether the adhesive is properly dotted; and generating an alarm signal in response to determining that the adhesive is not properly dotted.

23. The method of claim 22, further comprising responding to the alarm signal by replacing a source of the adhesive in equipment that dots the adhesive on the substrate.

* * * * *